(12) United States Patent
Ellis

(10) Patent No.: US 11,642,218 B2
(45) Date of Patent: *May 9, 2023

(54) INTRAOCULAR LENSES WITH SHAPE-CHANGING OPTICS AND STABILIZING PROPERTIES

(71) Applicant: JelliSee Ophthalmics Inc., McLean, VA (US)

(72) Inventor: Forrest J. Ellis, McLean, VA (US)

(73) Assignee: JELLISEE OPHTHALMICS INC., McLean, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/829,726

(22) Filed: Jun. 1, 2022

(65) Prior Publication Data

US 2022/0387169 A1 Dec. 8, 2022

Related U.S. Application Data

(60) Provisional application No. 63/196,347, filed on Jun. 3, 2021.

(51) Int. Cl.
*A61F 2/16* (2006.01)

(52) U.S. Cl.
CPC .......... *A61F 2/1635* (2013.01); *A61F 2/1624* (2013.01); *A61F 2/1648* (2013.01); *A61F 2002/169* (2015.04); *A61F 2002/1682* (2015.04); *A61F 2250/0003* (2013.01); *A61F 2250/0067* (2013.01)

(58) Field of Classification Search
CPC .... A61F 2/1635; A61F 2/1624; A61F 2/1648; A61F 2002/1681; A61F 2250/0003; A61F 2250/0018; A61F 2250/0019
See application file for complete search history.

(56) References Cited

U.S. PATENT DOCUMENTS

| | | | |
|---|---|---|---|
| 10,052,197 B2 | 8/2018 | Dolla et al. | |
| 2004/0169932 A1* | 9/2004 | Esch | A61F 2/1635 359/665 |
| 2007/0088433 A1* | 4/2007 | Esch | A61F 2/1648 623/6.37 |
| 2016/0157996 A1* | 6/2016 | Dolla | A61F 2/1635 623/6.15 |
| 2019/0053892 A1* | 2/2019 | Siney | A61F 2/16 |
| 2019/0269499 A1 | 9/2019 | Ellis | |
| 2019/0274823 A1* | 9/2019 | Argento | A61F 2/1635 |
| 2020/0345481 A1 | 11/2020 | Ellis | |
| 2022/0015892 A1 | 1/2022 | Ellis | |
| 2022/0015894 A1 | 1/2022 | Ellis | |
| 2022/0151768 A1 | 5/2022 | Ellis | |

* cited by examiner

*Primary Examiner* — Javier G Blanco
(74) *Attorney, Agent, or Firm* — Tarolli, Sundheim, Covell & Tummino LLP

(57) ABSTRACT

An intraocular lens (IOL) with a shape-changing optic is provided. The shape-changing optic includes an elastic anterior face located anterior to the equator. The anterior face has an anterior surface, a posterior surface, and a periphery. The shape-changing optic also includes a posterior face having an anterior surface, a posterior surface, and a periphery. An elastic side wall can extend across the equator and extend from the anterior face to the posterior face. A chamber can be located between the anterior face and the posterior face. The IOL can further include at least one haptic extending from the periphery of the anterior face, the periphery of the posterior face, or both.

18 Claims, 10 Drawing Sheets

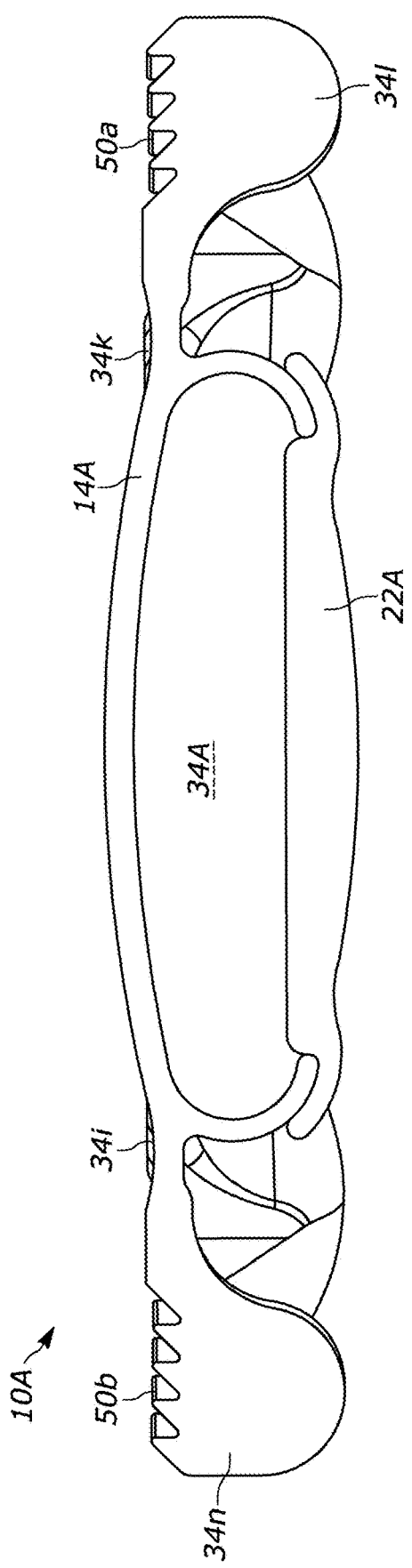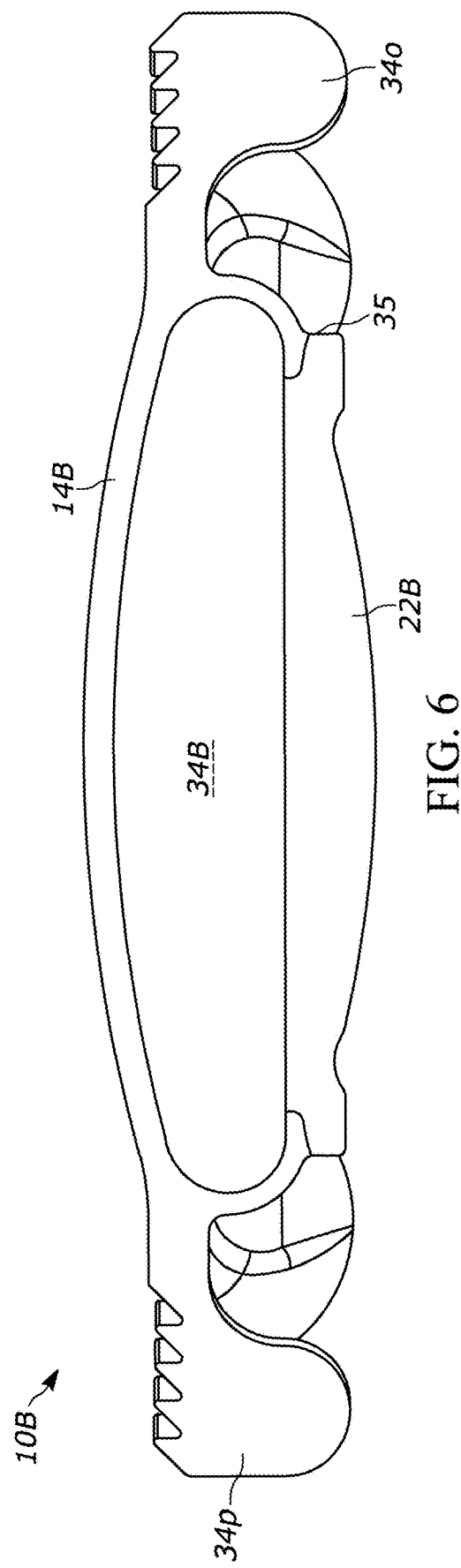
FIG. 5
FIG. 6

INTRAOCULAR LENSES WITH SHAPE-CHANGING OPTICS AND STABILIZING PROPERTIES

CROSS-REFERENCE TO RELATED APPLICATIONS

The present application claims priority to U.S. Provisional Application No. 63/196,347 filed on Jun. 3, 2021, which is incorporated by reference in its entirety.

TECHNICAL FIELD

The present disclosure relates to an accommodative intraocular lens that includes an optic that can change shape as the intraocular lens transitions from an accommodative state to a dis-accommodative state.

BACKGROUND

The lens of the eye constitutes cells arranged in a lamellar manner and is divided into a central nucleus and a peripheral cortex. The lens is enclosed by a cellular basement membrane (the lens capsule). Along with the cornea, the lens focuses light (refraction) onto the retina of the eye. Refractive power is measured in diopters. The lens contributes approximately a third of the refractive power of the eye and it is responsible for fine-tuning the eye's focus so that objects over a wide range of distances can be seen clearly. The process whereby the lens changes the focus of the eye is called accommodation. Accommodation is measured in diopters of accommodation change. Accommodation occurs with contraction of the ciliary muscle, which reduces force on the lens suspensory zonular fibers (zonules). The lens zonules extend from the ciliary muscle to the near equatorial regions of the lens and suspend the lens behind the iris. Reduction of force on the zonules allows the lens of the eye to assume its natural, less stressed, more spherical shape; thereby increasing it dioptric power, and this brings objects at near into focus. The change in focus from distance focus to near focus is generally smooth and controlled by a complex neural feedback mechanism. The relative contribution to accommodation of the lens zonules, the lens capsule, the lens nucleus and the surrounding lens cortex is the subject of ongoing research.

With age, there is a gradual reduction in the ability of the lens to alter the focus of the eye (presbyopia). This manifests in a gradual loss of capacity to focus on near objects, typically requiring optical assistance (e.g. reading glasses, bifocals) beginning around the fifth to sixth decades of life. There are many theories explaining accommodation and the loss of accommodation. It is generally accepted that with aging the lens substance itself becomes more resistant to deformational change (e.g. less pliable, more rigid, or firmer). A comprehensive and definitive understanding of accommodation and the cause(s) of presbyopia is still subject to scientific inquiry. However, much is already known regarding structural and functional changes of the lens and the other structures of the eye that contribute to accommodation and to the gradual loss of accommodation.

The ciliary muscle has been shown to function throughout life without significant loss of function with aging. The lens zonules include anterior fibers which attach to the lens anterior to the lens equator, equatorial fibers which attach at the lens equator, and posterior fibers which attach posterior to the lens equator. It has been demonstrated that the anterior fibers primarily alter the shape of the anterior lens surface and the posterior fibers primarily control the shape of the posterior lens surface. The sparse and less robust equatorial fibers play a lesser role in changing of the shape of the surfaces of the lens. Some conditions and genetic disorders may contribute to lens zonule loss or breakage, but in general the lens zonules remain functional throughout life. Therefore, changes in the lens zonules are not considered a significant factor in the loss of accommodation.

The lens nucleus and cortex are unique in that the cellular makeup and structure of the lens allows for reshaping of individual cells with intracellular flow of cytosol (the fluid within the cell). As a result, the individual cell shape can change and cumulatively the entire lens contents, contained within the lens capsule, can be considered a viscoelastic or "semi-flowable fluid". However, in youth, the lens nucleus is less resistant to deformational change (e.g. less firm or more pliable), than compared to the lens cortex. This is termed the lens elastic gradient. Studies have shown that with aging the lens nucleus becomes more resistant to deformational change (e.g. less pliable, or firmer). Likewise, studies show that the lens cortex also becomes more resistant to deformational change (e.g. less pliable or firmer with aging). However, the lens nucleus becomes firmer at a faster rate than the lens cortex. The crossover, where the nucleus becomes firmer, less pliable, or more resistant to deformational change than the lens cortex occurs around age 40-50 years of age. This relative change in the difference in firmness of the nucleus relative to that of the cortex correlates with the loss of accommodation and the onset of presbyopia.

The human crystalline lens can be affected by one or more disorders or conditions that reduces its function and/or reduces the clarity of the lens. A common condition that occurs with aging is the gradual opacification and reduced transparency of the lens of the eye. This condition is termed a cataract. Surgical removal of a cataractous lens and placement of an artificial replacement lens (such as an intraocular lens ("IOU") within the eye is a common surgical procedure. The development of a suitable IOL that can provide the optical quality and accommodation provided by the youthful biological lens has not been developed.

There are generally two classes of IOLs that have been developed that attempt to overcome the lack of accommodation of an IOL used to replace the natural lens when cataract surgery is performed: pseudo-accommodating lenses and accommodating lenses. A pseudo-accommodating lens can be a multiple focal point lens that uses a ring for distance focus and one or more center optics for intermediate and near focus. Other designs use diffraction optics to obtain a range of focus or use optics to achieve an extended depth of focus (EDOF). Multi-focus optics, diffraction optics, and EDOF optic IOLs can result in disruptive optical aberrations such as glare, halos, reduced contrast sensitivity, etc. Centration of these lenses within the capsular bag is important to their best visual function. These lenses use non-deforming optical elements and do not achieve the visual quality of a natural, youthful lens of the human eye. The accommodating class of IOLs includes a silicone elastomeric hinged lens that allows forward movement of the optic when the eye focuses at near. These lenses are typically placed in the lens capsular bag (the remaining thin layer of basement membrane that is the outermost layer of the natural lens and is typically left in place when the contents of the lens are removed during cataract surgery). Due to progressive fibrosis and stiffening of the lens capsule following cataract removal, the effective accommodation with these lenses is known to diminish over time.

Overall, these lenses may be adequate for distance and intermediate vision, but only provide accommodation of about two diopters at most and this value has been shown to diminish over time.

Shaped haptics, levers, or other mechanical elements have been described to translate the compressive force exerted by the elasticity of the lens capsule and/or the radial compressive force exerted by the ciliary muscles to effect a desired axial displacement of the IOL optic. Additional examples may also provide flexible hinge regions of the haptic to facilitate axial displacement of an IOL along the optical axis. Several examples include annular ring elements in contact with the lens capsule and that use the compression of applied force by the capsule to effect axial displacement of the IOL optic. However, these IOLs are configured to be generally of fixed optical power and in line with the optical axis of the eye. As such, the axial displacement of the optical elements of these IOLs that is possible limits the dioptric power change attained. Some single or multiple optic lenses have incorporated a shape changing and axial displacement changing combination of lenses, such as a shape changing optic coupled to zonular contact haptics whereby compression of the lens capsule during accommodation results in both anterior displacement of the flexible optic along the optical axis, as well as compression of the sides of the optic at the equator. Other described IOLs rely on a posterior flexible region separated from a flexible anterior lens by an articulating member about the circumference.

It is known that the lens capsule, following cataract surgery, becomes less pliable and more fibrotic. IOLs that rely on retained capsular elasticity/pliability are unlikely to retain accommodating/dis-accommodating ability.

Surface shape changing lenses are more likely to result in greater degrees of dioptric power change. These lenses include lenses with fluid filled chambers that rely on compression by the lens capsule along the optical axis to force fluid from a peripheral chamber into a central lens and thereby change the shape of the central lens and therefore the optical power of the lens. Other lenses use the compressive force by the lens capsule to provide a radial inward compressive force about the equatorial periphery of a flexible lens to shape change the lens. These are generally two-part systems with a circumferential haptic design with a central fixed posterior lens that fits within the capsule and then a separately placed pliable optic secured within the outer haptic ring. Compression by the "elastic" lens capsule is meant to provide a compressive force to the central lens flexible optic. Other IOLs use a compressive force exerted on rigid haptics to compress a pliable optic against a separate fixed power posterior lens. These IOLs rely on the shape change of the posterior surface of the pliable optical element pressed against a fixed optical element or pressed against a relatively rigid posterior lens capsule to alter the dioptric power of the lens system. Other IOLs incorporate a skirt with a capsular contact ring. Such IOLs rely on compression exerted by the "elastic" lens capsule to impart a compressive force on a capsular contact ring and the mechanical design of this ring pulls radially about the equator of the IOL's flexible optic. Again, because these IOLs rely on retained capsular elasticity/pliability and because it is generally known that the lens capsule following cataract surgery becomes less pliable and more fibrotic, it is unlikely these lenses will retain accommodating/dis-accommodating ability. None of the shape changing accommodating IOLs described above mimic the natural human lens during accommodation or effectively account for the inevitable loss of capsular elasticity/pliability and progressive fibrosis and stiffening of the lens capsule.

SUMMARY

The present disclosure relates to ophthalmic devices including IOLs and more particularly to accommodating intraocular lenses (accommodating IOLs). In an aspect, an IOL can comprise a shape-changing optic configured for placement in or adjacent to a lens capsule. The IOL has an optical axis extending in an anterior-posterior direction, an equator extending in a plane substantially perpendicular to the optical axis, an accommodated state, a dis-accommodated state, and states therebetween. The IOL can comprise an elastic anterior face located anterior to the equator, having an anterior surface, a posterior surface, and a periphery having a plurality of extension sites. The IOL can also include a posterior face located posterior to the equator, having an anterior surface defining an annular channel, a posterior surface, and a periphery. An elastic side wall can extend across the equator and extend from the anterior face to the posterior face. The elastic side wall can have a posterior edge complimentary to and non-releasably bonded to the annular channel of the posterior face. A chamber can be located between the anterior face and the posterior face and can contain a material. The anterior face can be more resistant to deformational change than the material. The IOL can further include a plurality of haptics each having a medial portion and a lateral portion, the medial portion of each of the plurality of haptics extending from and connected to a respective extension site of the plurality of extension sites of the periphery of the anterior face.

In an aspect, an IOL can comprise a shape-changing optic configured for placement in or adjacent to a lens capsule. The IOL has an optical axis extending in an anterior-posterior direction, an equator extending in a plane substantially perpendicular to the optical axis, an accommodated state, a dis-accommodated state, and states therebetween. The IOL can comprise an elastic anterior face located anterior to the equator, having an anterior surface, a posterior surface, and a periphery having a plurality of extension sites. The IOL can also include a posterior face located posterior to the equator, having an anterior surface, a posterior surface, and a periphery. An elastic side wall can extend across the equator and extend from the anterior face to the posterior face. A chamber can be located between the anterior face and the posterior face and can contain a material. The anterior face can be more resistant to deformational change than the material. The IOL can further include a plurality of haptics each having a medial portion and a lateral portion, the medial portion of each of the plurality of haptics extending from and connected to a respective extension site of the plurality of extension sites of the periphery of the anterior face. The IOL can include a plurality of arches, each of which is located at a respective extension site.

BRIEF DESCRIPTION OF THE DRAWINGS

FIG. 5 is a side view of an IOL according to an aspect of the present disclosure.

FIG. 6 is a side view of an IOL according to another aspect of the present disclosure.

DETAILED DESCRIPTION

Figure 1:
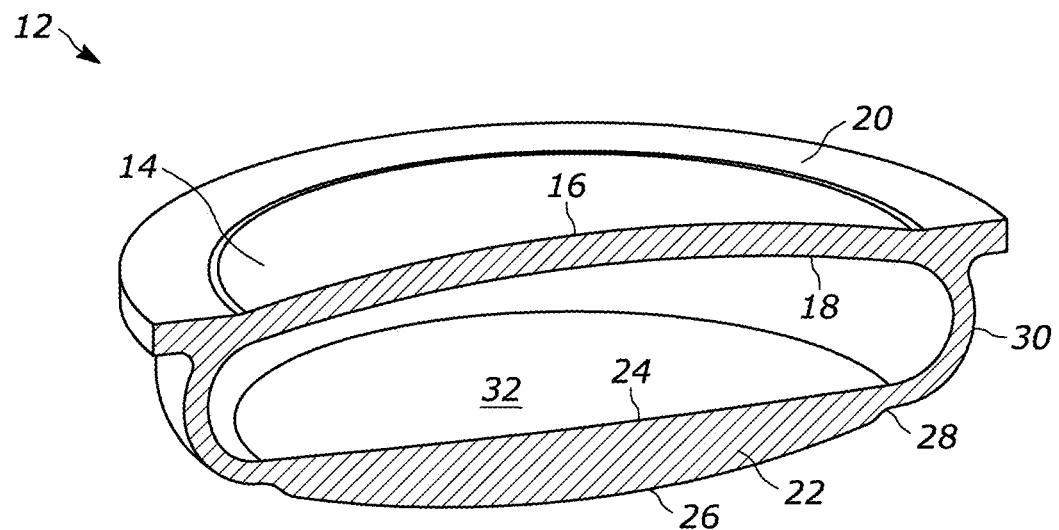
FIG. 1 is a perspective cross-sectional view of a shape-changing optic of an IOL according to an aspect of the present disclosure.

The present disclosure relates to an IOL such as, for example, an accommodative IOL. As used herein with respect to a described element, the terms "a," "an," and "the" include at least one or more of the described element(s) including combinations thereof unless otherwise indicated. Further, the terms "or" and "and" refer to "and/or" and combinations thereof unless otherwise indicated. By "substantially" is meant that the shape or configuration of the described element need not have the mathematically exact described shape or configuration of the described element but can have a shape or configuration that is recognizable by one skilled in the art as generally or approximately having the described shape or configuration of the described element. As used herein, the terms "anterior," "posterior," "superior," "inferior," "lateral," and "medial" refer to the position of elements when a patient is in a standard anatomical position unless otherwise indicated. The terms "left," "right," "top" and "bottom" refer to the position of elements as they are depicted in the drawings and the terms "left" and "right" can be interchanged unless indicated otherwise. The terms "first," "second," etc. are used to distinguish one element from another and not used in a quantitative sense unless indicated otherwise. Thus, a "first" element described below could also be termed a "second" element. A component operably coupled to another component can have intervening components between the components so long as the IOL can perform the stated purpose. By "integral" or "integrated" is meant that the described components are fabricated as one piece or multiple pieces affixed during manufacturing or the described components are otherwise not separable using a normal amount of force without damaging the integrity (i.e. tearing) of either of the components. A normal amount of force is the amount of force a user would use to remove a component meant to be separated from another component without damaging either component. As used herein a "patient" includes a mammal such as a human being. All IOLs as described herein are used for medical purposes and are therefore sterile. Components of IOLs as described herein can be used with IOLs described herein as well as other IOLs. For example, an IOL as described herein can be placed anterior to an existing, previously placed IOL. IOLs include fixed power, multifocal, EDOF, diffractive and other variable focus lenses. Although the drawings show certain elements of an IOL in combination, it should be noted that such elements can be included in other embodiments or aspects illustrated in other drawings or otherwise described in the specification. In other words, each of the disclosed aspects and embodiments of the present disclosure may be considered individually or in combination with other aspects and embodiments of the disclosure including patent applications incorporated by reference herein.

Unlike shape changing accommodating IOLs described by way of background, IOLs are provided herein that can mimic the gradient elastic properties of a natural youthful human lens during accommodation and include a shape-changing optic where components of the optic change shape as the IOL transitions from an accommodated state to a dis-accommodated state and vice versa. Without wishing to be bound by a specific mechanism of action, it is considered by some that the lens capsules' "elasticity" controls and shapes the lens as a whole (the lens nucleus and cortex). On this basis, the lens contents are considered pliable. However, the volume of the lens contents compared to the thickness and known modulus of elasticity of the lens capsule predicts that the lens capsule cannot solely control and alter the shape of the lens nucleus and cortex. Finite element analysis (FEA) predicts that radial tension about the equatorial region of a lens capsule filled with a soft pliable solid or liquid does not result in significant shape change to either the anterior or posterior surface of the lens compared to what is known to occur with the natural youthful human lens. Providing radial tension directed specifically to at least the anterior face of an accommodating IOL; having that tension directed at points anterior to the equator of the IOL; the anterior face of the IOL being more resistant to deformational change than the content(s) of a chamber underlying the anterior face; the anterior face demonstrating elastic properties in so much as the anterior face deforms when a force is applied to the anterior face and the anterior face will return to its original shape with the removal of the force, results in a greater amount of anterior face shape change and therefore accommodating dioptric power change than can be achieved with a similar force applied at points at or more near the equator of the IOL (e.g. equatorial). In addition, a force applied to the anterior face at points anterior to the equator of the IOL requires less diameter change of the anterior face per diopter of power change of the IOL compared to a similar force applied at points at or more near the equator of the IOL thereby allowing the anterior face of the IOL to shape change even with very small amounts of anterior face diameter change when going from an accommodated state, a dis-accommodated state, and states in between.

In particular, in an aspect, an IOL comprising a shape changing optic that can assume an accommodated state, a dis-accommodated state, and states therebetween is provided. Components of the shape-changing optic can be deformable such that radially directed ocular compression force(s) or tensile force(s) applied to the optic caused by ciliary muscle contraction or relaxation causes one or more components of the optic to change shape and allows the optic to change dioptric power. None of the described IOLs above apply a radially outward tensile force that is directly transferred to the anterior surface at point(s) anterior to the equator of the optic.

Figure 2:
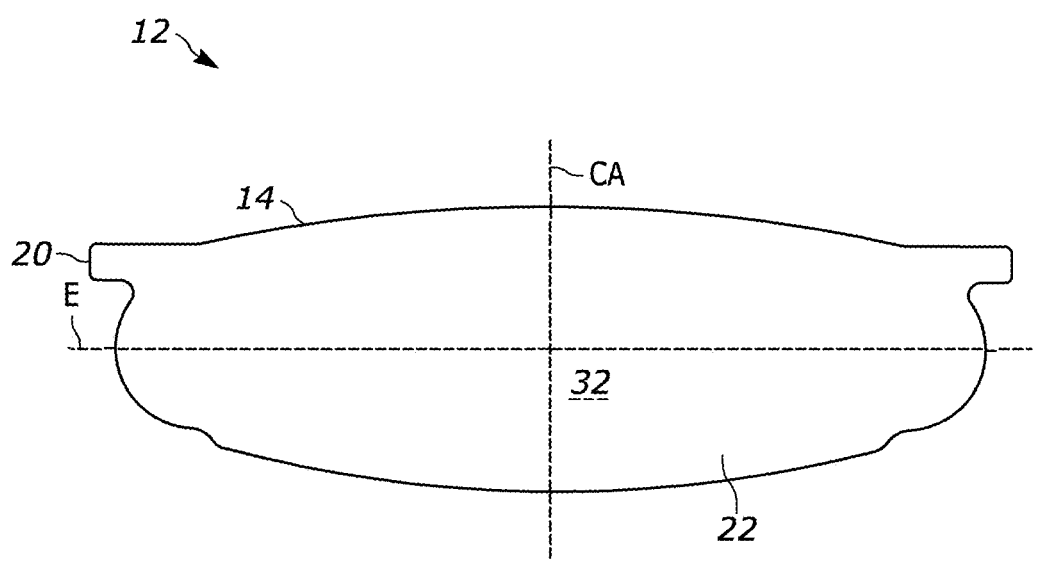
FIG. 2 is a side view of a shape-changing optic of an IOL according to an aspect of the present disclosure.
Figure 3:
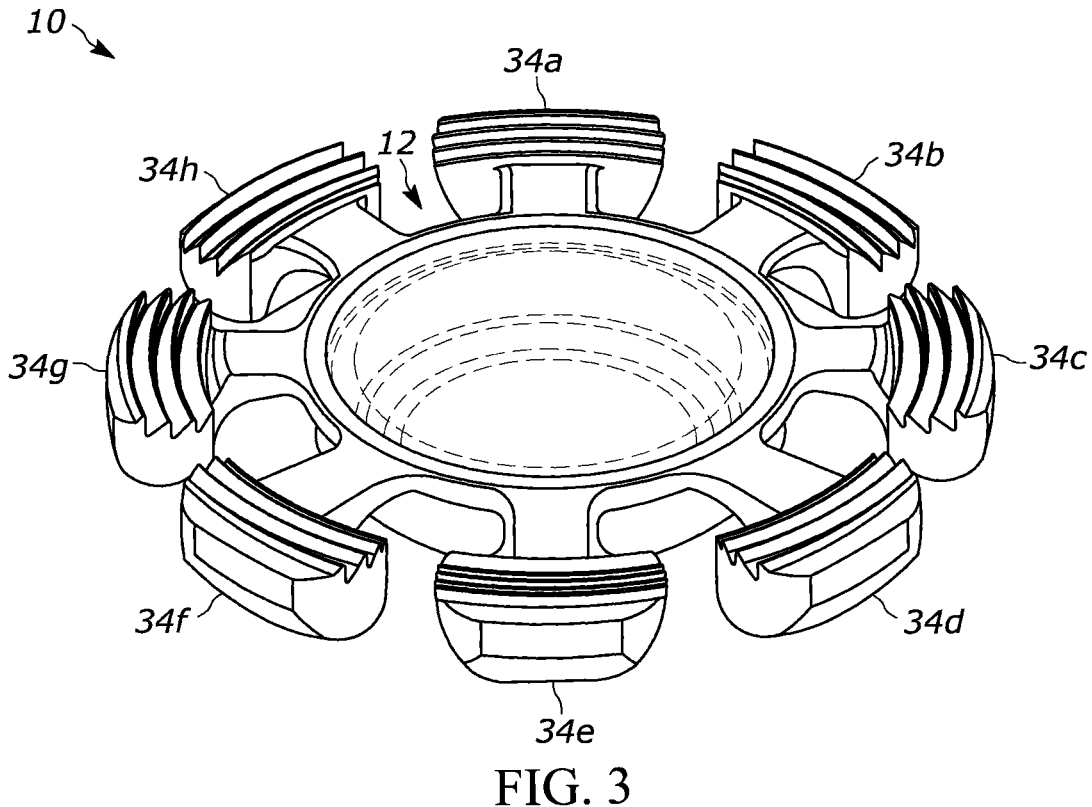
FIG. 3 is a perspective view of the IOL including the shape changing optic of FIGS. 2 and 3 including a depiction of haptics according to an aspect of the present disclosure.

As such, components of a shape-changing optic can deform or change shape when a force is applied. If a component is less resistant to deformational change than another component, the former component is more likely to, or to a greater degree, deform for a given amount of applied or removed force than the latter component. A component is more resistant to deformational change than another component, if the former component is less likely to, or to a lesser degree, deform for a given amount of applied or removed force than the latter component. It is understood that for any given component resistant to deformational change, the force applied/removed to such component does not exceed the force that results in breakage of the component such that it is no longer useful for its therapeutic purpose. FIG. 2 depicts a central or optical axis CA extending in an anterior-posterior direction and an equator E extending in a plane substantially perpendicular to the central axis. The equator is an imaginary line drawn around the circumference of a lens perpendicular to the optical axis, equally distant from the anterior face of the lens and the posterior face of the lens, dividing the lens into an anterior half and a posterior half. Referring to FIGS. 1-3, a shape-changing optic 12 of an IOL 10 can comprise an elastic anterior face 14 located anterior to equator E. Anterior face 14 can have an anterior surface 16, a posterior surface 18 and a periphery 20. Shape-changing optic 12 can also comprise a posterior face 22 having an anterior surface 24, a posterior surface 26, and a periphery 28. Shape-changing optic 12 can further include an elastic side wall 30 extending across equator E and extending from anterior face 14 to posterior face 22. A chamber 32 can be located between anterior face 14 and posterior face 22 and can house material or contents as described in more detail below. Components of the shape-changing optic can be made to be more or less resistant to deformational change by altering the thickness of the component, the type of material from which the component is fabricated, or by altering the chemical/material properties of the component material itself for example. With reference to FIG. 3, IOL 10 can further comprise at a plurality of haptics 34 extending from the periphery of the anterior face. A plurality of haptics can also extend from the periphery of the posterior face, or the periphery of both the anterior face and the posterior face as described below.

Regarding specific components of an IOL, the anterior face, as stated above, can have elastic properties. Elastic properties can allow for the anterior face to change shape with an applied force, but also to return to its original configuration when the force is removed. It is beneficial that the anterior face be more resistant to deformational change (e.g. less pliable, firmer) than the contents or material contained within the chamber because when an outward radial force is applied to the anterior face, the contents of the chamber can more easily deform to allow flattening of the anterior face. Exemplary fabrication materials for the anterior face include silicone, an acrylic (hydrophobic or hydrophilic) polymer, polymethylmethalcryalate (PMMA), silastic, collamer, a suitable optical thermoplastic polymer, another suitable optical material, and suitable combinations thereof. The anterior face can comprise a lens with a variety of optical properties, such as, for example, a spherical, aspheric, toric, toroidal, multifocal, diffractive, extended depth of focus, or combinations thereof.

Figure 4:
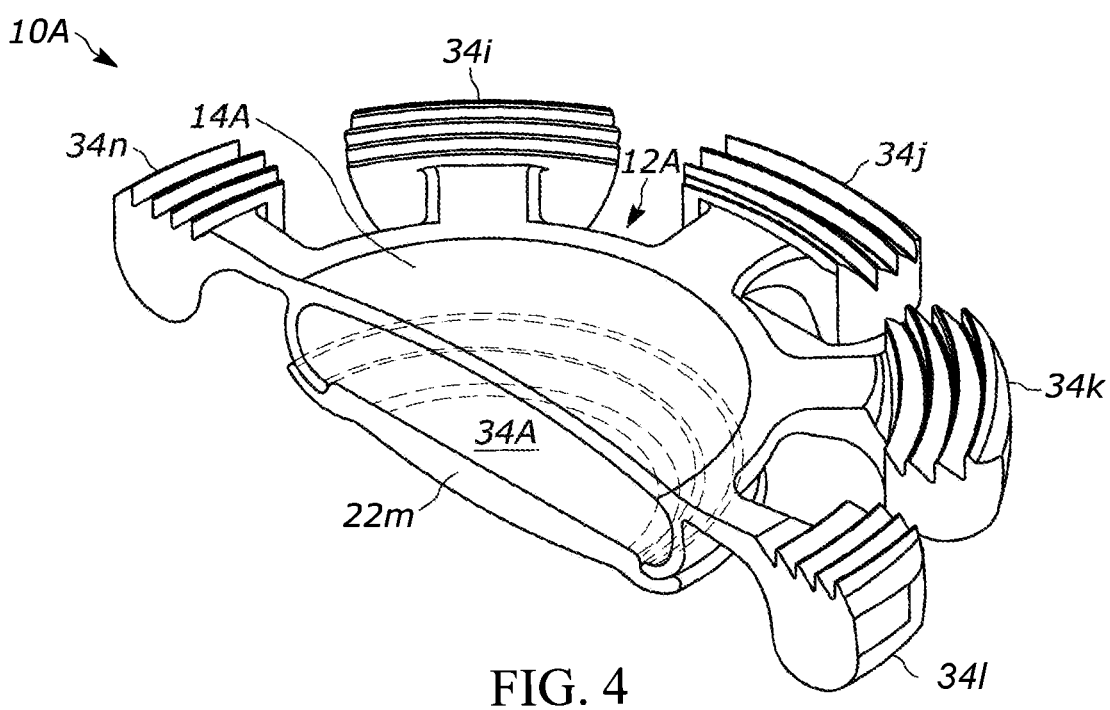
FIG. 4 is a perspective cross-sectional view of an IOL according to another aspect of the present disclosure.

Regarding the posterior face of the shape-changing optic, the posterior face can be more resistant to deformational change than the anterior face or the contents contained within the chamber of the shape-changing optic. The posterior face need not have the ability to change shape. When implanted and in certain aspects, the posterior face can rest against the posterior capsule and the vitreous substance and it may not be desirable to have those less predictable forces altering the power of the optic. Furthermore, having a posterior face that is more resistant to deformational change than the anterior face or the contents of the chamber of the shape-changing optic can allow the posterior face optic to have a relatively more fixed power posterior lens permitting the incorporation of beneficial optical properties. In addition, a posterior face more resistant to deformational change can allow the contents of the chamber to reshape the side wall(s) when the anterior face changes shape in response to a force. The posterior face can be part of a one-piece integral IOL 10 as depicted in FIG. 1-3 or can be a two-piece integral IOL 10A as illustrated in FIG. 4-6. In certain aspects, the posterior face is elastic. Exemplary fabrication materials for the posterior face include silicone, an acrylic (hydrophobic or hydrophilic) polymer, polymethylmethalcryalate (PMMA), silastic, collamer, a suitable optical thermoplastic polymer, another suitable optical material, or suitable combinations thereof. The posterior face can comprise a lens with a variety of optical properties, such as, for example, a spherical, aspheric, toric, toroidal, multifocal, diffractive, extended depth of focus, or combinations thereof. As illustrated in FIG. 6, an IOL 10B can comprise a shape-changing optic where the posterior face 22B has a squared peripheral edge 35 to reduce posterior capsular opacification, by inhibiting, for example, peripheral lens epithelial cells from migrating across the posterior face.

Figure 7:
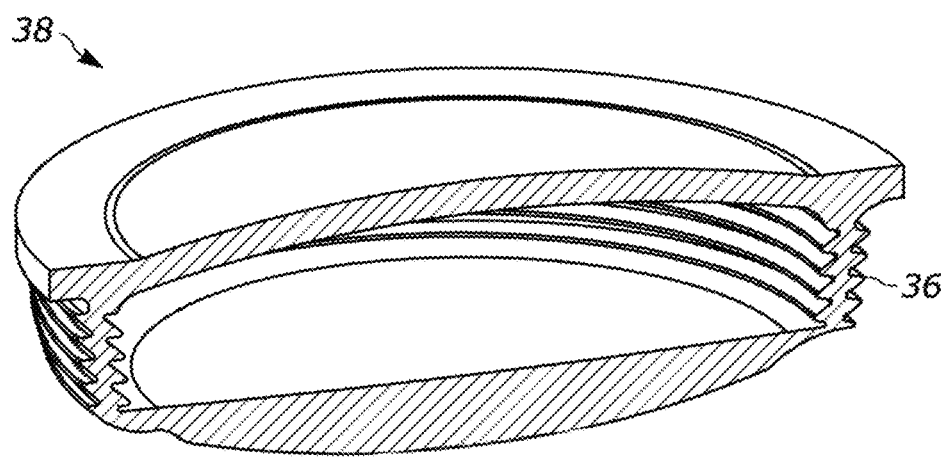
FIG. 7 is a perspective cross-sectional view of a shape-changing optic of an IOL according to an aspect of the present disclosure.
Figure 8:
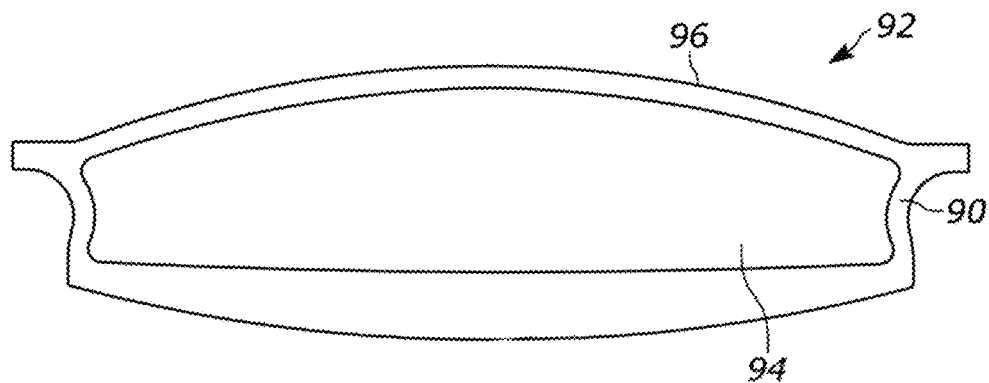
FIG. 8 is a side cross-sectional view of a shape-changing optic of an IOL according to an aspect of the present disclosure.

Regarding the side wall, as stated above, the side wall can have elastic properties. In certain aspects, the side wall can be fabricated from a material that is equal to or less resistant to deformational change than the anterior face. Such features can allow for the contents contained within the chamber to expand the area of the side wall to allow the volume of the contents of the chamber to remain the same when the anterior surface is flattened. Having the side wall deform can facilitate and allow for a greater amount of shape change to the anterior face of the shape-changing optic. Exemplary fabrication materials for the side wall include silicone, an acrylic (hydrophobic or hydrophilic) polymer, polymethylmethalcryalate (PMMA), silastic, collamer, a suitable optical thermoplastic polymer, another suitable material, or a suitable combination thereof. The side wall can also be equal to or less resistant to deformational change than the anterior face or the posterior face by being thinner than the anterior face or the posterior face. Alternatively, or in addition, the side wall 36 of a shape-changing optic 38 can be equal to or less resistant to deformational change by having a bellowed configuration as illustrated in FIG. 7. The bellows can be horizontally or vertically oriented or have other orientations to allow for peripheral side wall expansion or contraction. As illustrated in FIG. 8, the side wall 90 of a shape changing optic 92 can have a plano, concave, convex, or other configuration to facilitate displacement of the contents of chamber 94 against side wall 90 when anterior face 96 is flattened.

Figure 9:
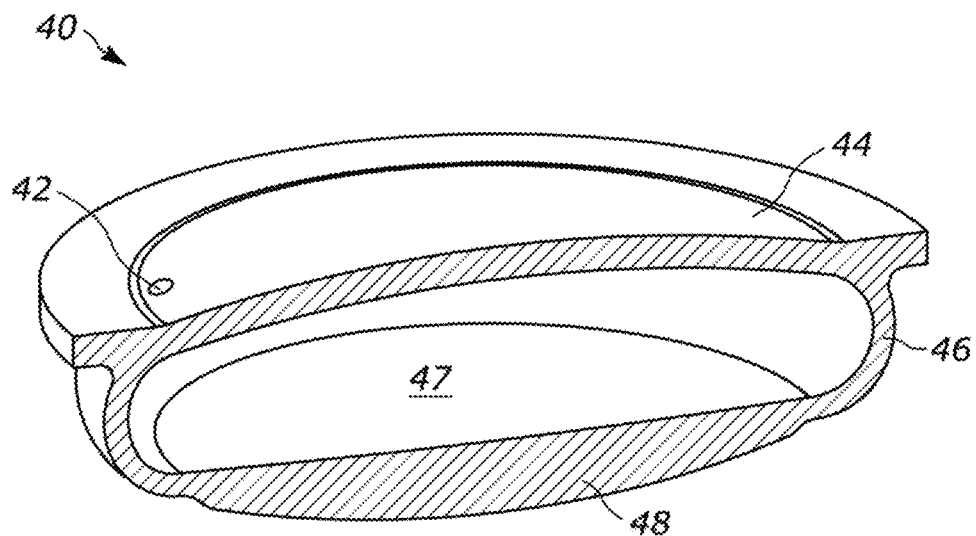
FIG. 9 is a is a side cross-sectional view of a shape-changing optic of an IOL according to an aspect of the present disclosure

Regarding the chamber, the chamber can be defined by the posterior surface of the anterior face, the anterior surface of the posterior face, and an inner surface of the side wall. The interior contents or material of the chamber can comprise a soft solid, a gel, a viscoelastic material, a flowable fluid, or a gas, or other suitable material. Exemplary materials that can be contained within the interior of the chamber include a soft silicone, or other soft material subject to deformational change, air or other gas, silicone oil (of various refractive indices), an aqueous solution of saline or hyaluronic acid, a viscoelastic polymer, polyphenyl ether, or other optical fluid, solid or gases, or suitable combinations thereof. The chamber can have an internal layer or coating, such as a parylene coating for example, to seal the contents of the chamber from the anterior face, the side wall and/or the posterior face. The chamber can be pre-loaded (e.g. by a manufacturer) with a suitable material. Alternatively, the chamber can be loaded with a suitable material by a clinician. For example, and with reference to FIG. 9, a shape-changing optic 40 of an IOL can define at least one port 42 (enlarged in FIG. 9 for purposes of clarity) sized and dimensioned to receive a needle or catheter, the needle or catheter being sized and dimensioned to deliver a fluid, gel, or gas to the chamber and/or to exchange fluid with a different material or a material having a different refractive index, for example. Although FIG. 9 illustrates the port defined by anterior face 44, the port can be defined by the side wall 46 or the posterior face 48 of the shape-changing optic. Having a port can allow a user to add or remove substance from chamber 47 to adjust the optical power of the lens. For example, by adding additional substance to the chamber, the volume of the substance can increase in the chamber resulting in an increase in the surface(s) curvature and the overall power of the lens and removing substance can decrease the volume of the substance in the chamber resulting in a decrease in the surface(s) curvature and the overall power of the lens. Also, by exchanging the substance for one with a different refractive index, the overall dioptric power and the range of accommodation of the IOL can be increased or decreased.

Regarding the plurality of haptics of the IOL, such haptics are the portion of the IOL that are configured to interact with the lens capsule, the lens zonules, the ciliary muscle, or other parts of a patient's eye. The plurality of haptics can be molded, shaped into, integral with, or otherwise extend from the shape-changing optic of an IOL. The plurality of haptics can be elastic but can be more resistant to deformational change than the anterior face. An advantage to this is that the haptics can be firmer to provide a linear, radially directed force from the haptic that is directly transferred to the periphery of the anterior face. Without wishing to be bound by any particular mechanism of action, if the haptics were less resistant to deformational change than the anterior face, the radial tension could result in stretching of the haptics and less tension on the periphery of the anterior face. Thus, the anterior face may not shape change as much for a given force applied to the haptics. Exemplary fabrication materials for the haptics include silicone, an acrylic (hydrophobic or hydrophilic) polymer, polymethylmethalcryalate (PMMA), silastic, collamer, a suitable optical thermoplastic polymer, another suitable material, or suitable combinations thereof.

FIGS. 3 to 6 illustrate an IOL where a plurality of haptics extends from the anterior face of a shape-changing optic. The shape-changing optic can change shape in response to an ocular force, specifically a force generated by the contraction or relaxation of the ciliary muscle of the patient's eye. The plurality of haptics, interacting with the lens capsule, can apply radial outward tension to the anterior face when the ciliary muscle relaxes and radial outward tension is placed on the lens capsule via the lens zonules. The plurality of haptics can be elastic but can be equal to or more resistant to deformational change than the anterior face.

Figure 10:
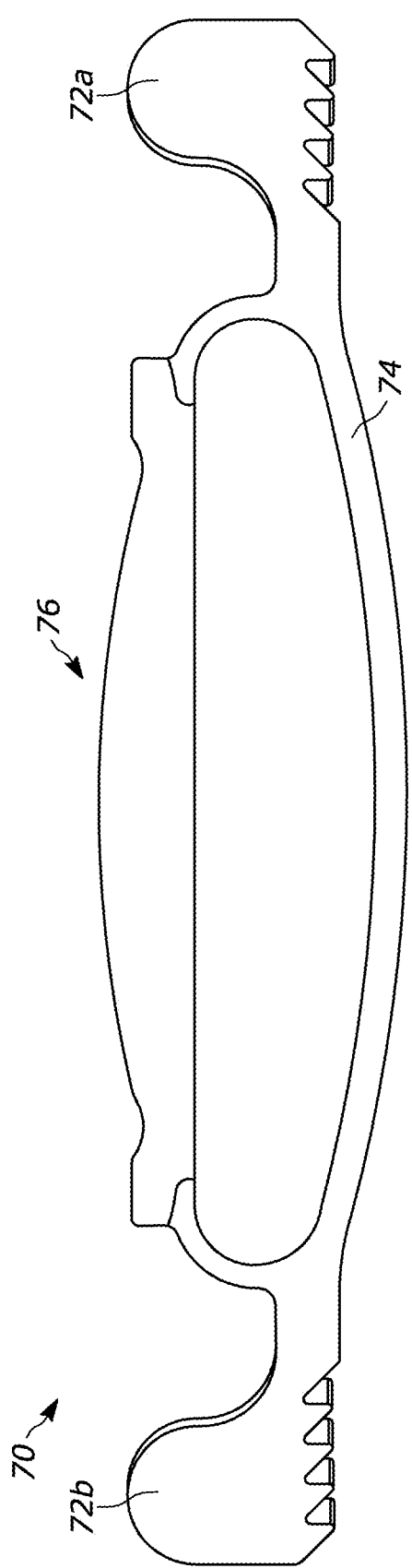
FIG. 10 is a side view of an IOL according to another aspect of the present disclosure.
Figure 11:
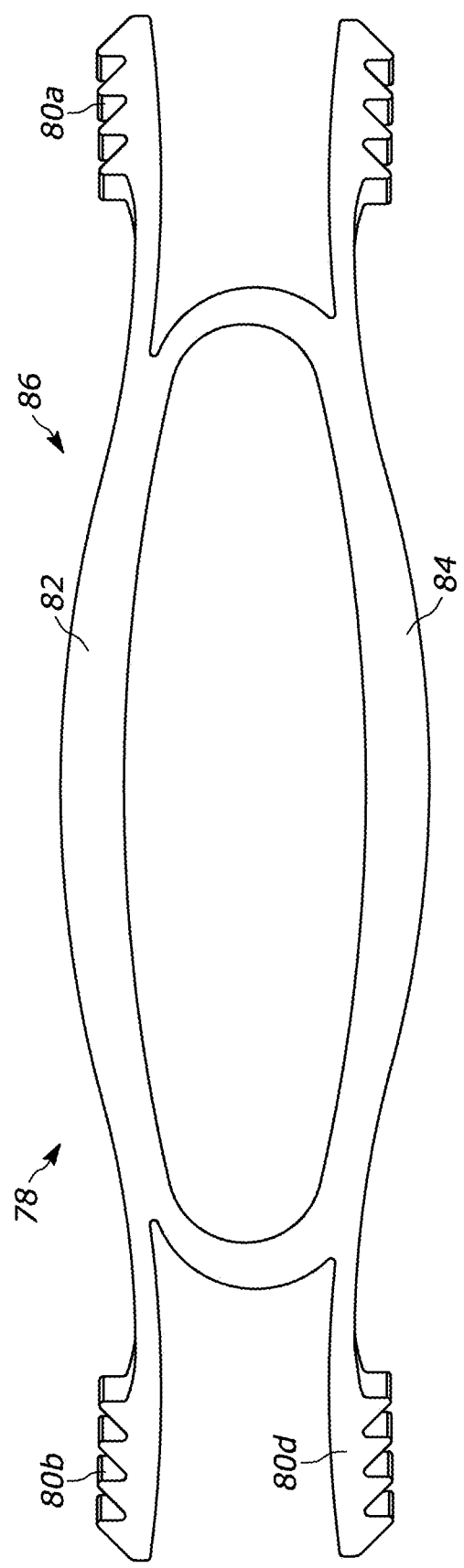
FIG. 11 is a side view of an IOL according to another aspect of the present disclosure.

FIG. 3 illustrates an aspect where a plurality of haptics extends circumferentially from the shape-changing optic. When implanted and when the ciliary muscles of a patient's eye relaxes (such as when the eye is in a dis-accommodated state), the ciliary muscles apply tensile force to the plurality of haptics (via the lens capsule with lens zonule attachments between the lens capsule and the ciliary muscles, for example). The plurality of haptics, in turn, can apply tensile force to the periphery of the anterior face at each site (referred to herein as an "extension site") where a respective haptic extends from the periphery of the anterior face. By having a plurality of haptics as depicted in FIGS. 3 and 4, the net result can be that the anterior face can be pulled radially outward substantially perpendicular to the optical axis from several extension sites (such as, for example, eight extension sites as illustrated in FIG. 3) and functionally result in relatively symmetric radial tension placed on the periphery of the anterior face of the shape-changing optic. Referring to FIG. 10, in certain aspects, an IOL 70 includes a plurality of haptics 72 extending from posterior face 74 of shape-changing optic 76. By having the force applied to the posterior face, a change in shape of the optic can be achieved independent of or in combination with a force applied to the anterior face. Referring to FIG. 11, in other aspects, an IOL 78 includes a plurality of haptics 80 extending from anterior face 82 and posterior face 84 of shape-changing optic 86. If a force is applied to both the posterior and the anterior faces, the total dioptric power change of the IOL for a given force can be increased. In other words, if a force is applied to both the anterior and posterior face, shape change can be obtained to both surfaces and thereby increase overall accommodation.

The plurality of haptics can engage the inner surface of the lens capsule or the outer surface of the lens capsule. Referring to FIGS. 3-6, the peripheral portion of the plurality of haptic 34 can comprise fixation members such as ridges 50 or other alternating raised and recessed areas as illustrated in FIGS. 3-6 configured to engage an inner surface of a lens capsule. For example, ridges 50 or alternating raised and recessed areas, etc. can interact with the lens capsule to stabilize the haptics within the lens capsule. Alternating raised and recessed areas can also allow the haptics to interact and fixate into the lens capsule. Such an aspect can allow IOL placement within the capsular bag, while still allowing translation of tension/relaxation of the lens capsule (via the lens zonules and ciliary body) during accommodation/dis-accommodation of the lens. Current haptic designs do not allow the haptics to be positioned into the lens capsule while fixating the haptics to allow tension/relaxation on the lens capsule to translate forces into the haptics. Current haptic designs are smooth and allow the capsule and haptic to glide past each other, which does not allow the translation of forces placed on the peripheral lens capsule (via the zonules and ciliary muscle). When placing the IOL inside the capsular bag, the ridges/dimples or other alternating areas of raised and recessed areas on the haptics fixate the lateral portions of the haptics to the inside periphery area/portion of the lens capsule. The alternating areas of raised and recessed areas then provide resistance to the lens capsule gliding radially outward over the peripheral haptic and facilitates the forces from the ciliary body, zonules, and lens capsule into a force on the haptics.

Figure 12:
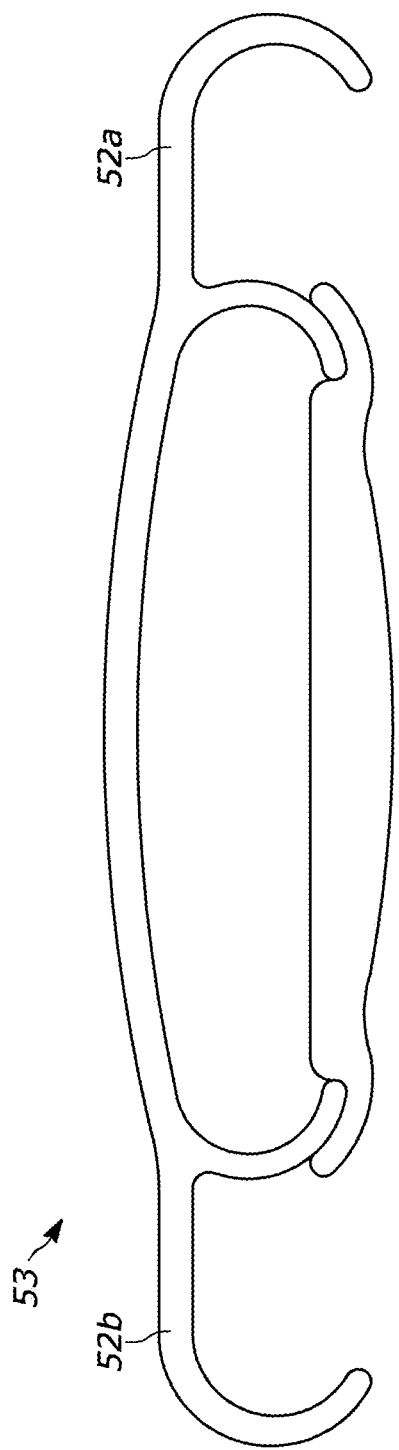
FIG. 12 is a side view of an IOL according to another aspect of the present disclosure.

Regarding the plurality of haptics engaging the outer surface of the lens capsule, when an IOL is placed anterior to an existing, previously implanted IOL, or when placed anterior to the lens capsule, the haptics can engage the outer surface of the lens capsule. Referring to FIG. 12, the peripheral portion of haptic 52 of an IOL 53 can comprise a hook-shaped/substantially J-shaped configuration to engage or curve around an outer surface of a lens capsule. The peripheral end of the peripheral portion can be an atraumatic end so that it does not damage zonules or the lens capsule. Each of the plurality of haptics can comprise a hook. Hook or substantially J-shaped haptics can allow an IOL to use the force translated from the ciliary muscle to the lens capsule, via the lens zonules, without requiring placement of haptics against elements of the ciliary muscle. Such an embodiment can avoid known potential complications of haptics placed against the ciliary muscle, such as uveitis, glaucoma, and bleeding (e.g. hyphema). Such an embodiment can be implemented in patients that have an already implanted IOL or patients that do not have an already implanted IOL.

Figure 13:
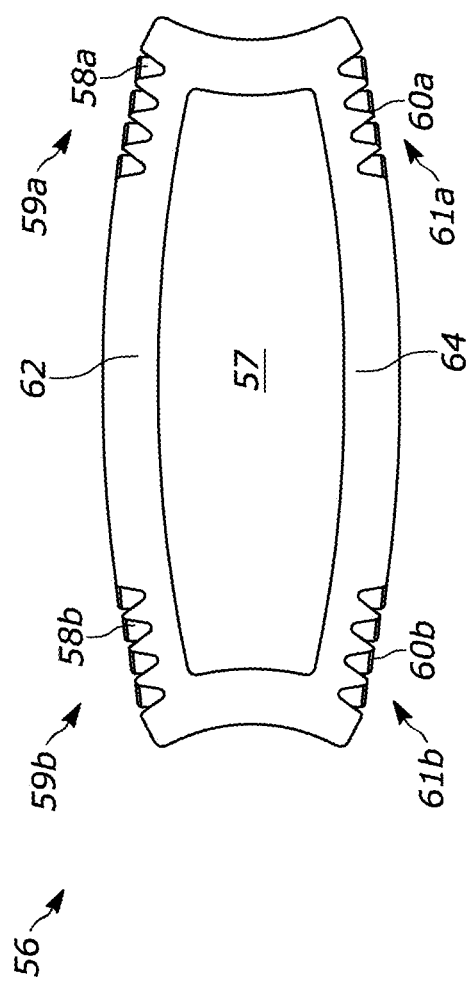
FIG. 13 is a side view of a shape-changing optic of an IOL according to an aspect of the present disclosure.

Referring to FIG. 13, the shape-changing optic itself can define ridges to engage the inner surface of a lens capsule. For example, the shape-changing optic 56 can include an expandable chamber 57, that has an integrated haptic with ridges 58 and 60 on periphery 59 of the anterior face 62 and/or the periphery 61 of the posterior face 64. When tension is placed on the lens capsule by the zonules (e.g. when the ciliary muscle relaxes), the force can be translated (by the ridges engaging the capsule) specifically to the anterior and posterior faces and not just translation of a general force to the entire lens. The anterior face, the posterior face, and/or the side walls can be more resistant to deformational change than the contents of the chamber. This configuration can allow forces from the lens capsule to provide radial tension to the haptics and thus to the anterior face, the anterior face being anterior to the equator of the lens; and/or to provide radial tension to the posterior face, the posterior face being posterior to the equator of the lens. The side walls can be configured to allow for the material in the chamber displaced by the flattening of the anterior face and/or the posterior face to expand into the area of the side wall, thereby allowing the volume of material within the chamber to remain the same.

Figure 14:
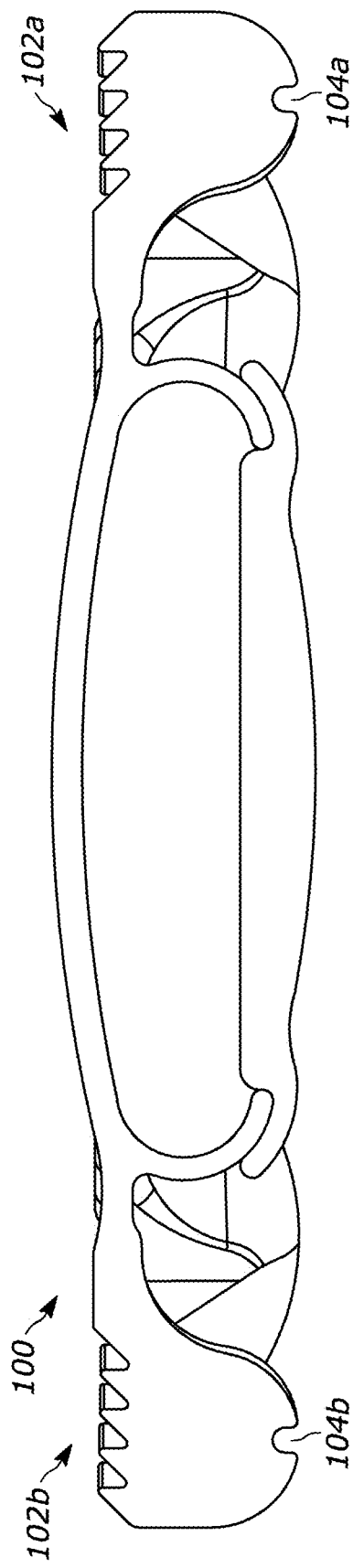
FIG. 14 is a side view of an IOL according to another aspect of the present disclosure.
Figure 15:
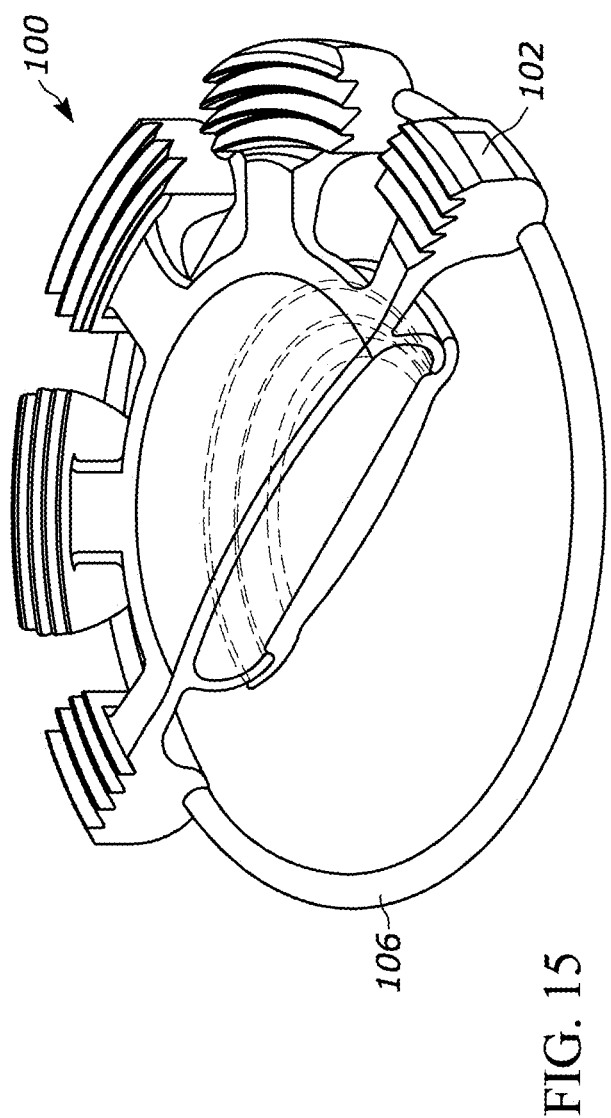
FIG. 15 is a perspective cross-sectional view of the IOL of FIG. 14 according to an aspect of the present disclosure.

Referring to FIGS. 14 and 15, in certain aspects, an IOL 100 is provided where the bottom of haptic 102 defines a recess 104. Such a recess can accommodate a stabilizing ring 106, for example, to keep the haptics from holding inwards with lens capsule fibrosis. Stabilizing ring can be fabricated from any of the materials described above with respect to the anterior and/or posterior faces of the shape changing optic.

In certain aspects, the haptics can contain a therapeutic agent. Non-limiting examples of therapeutic agents include an intraocular steroid, an antibiotic to mitigate post-operative inflammation/infection such that tear drops may not be necessary, a therapeutic agent for improving glaucoma or macular degeneration, or combinations thereof. For example and with respect to chronic conditions such as glaucoma or macular degeneration, the therapeutic agent can be placed in the recessed areas of the haptics (in embodiments having such recessed areas) for long-term of sustained release of the therapeutic agent.

Figure 16:
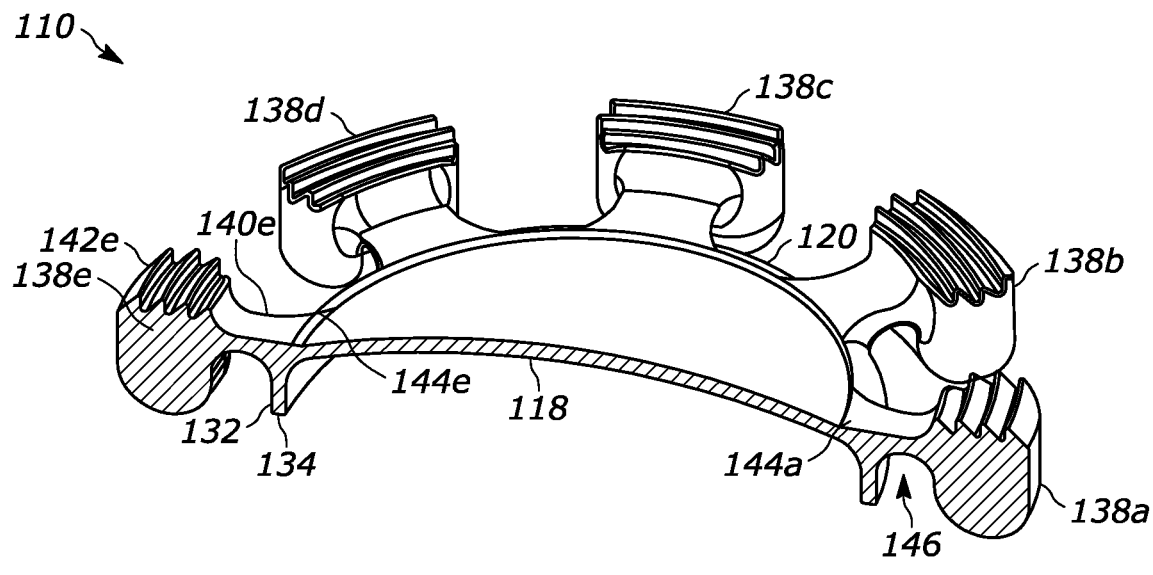
FIG. 16 is an exploded view of an IOL according to an aspect of the present disclosure.
Figure 16:
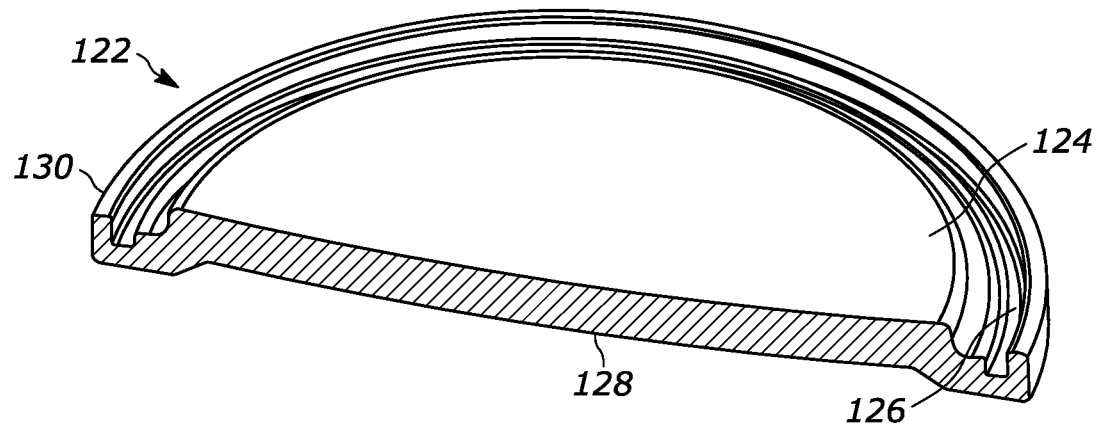
Figure 17:
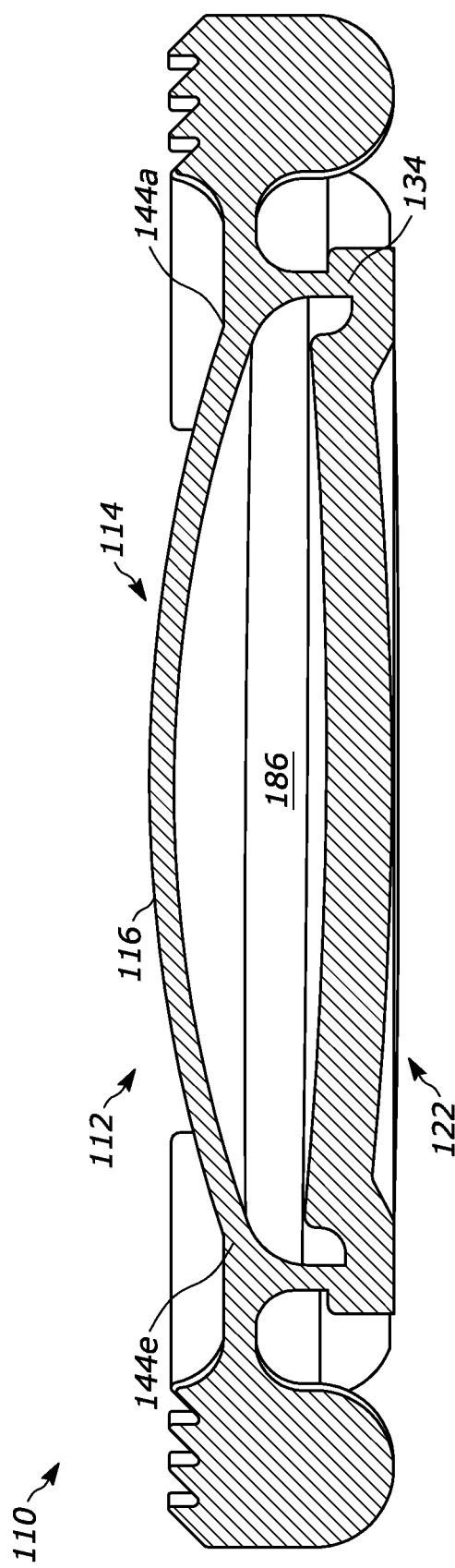
FIG. 17 is a side view of an IOL according to an aspect of the present disclosure.
Figure 18:
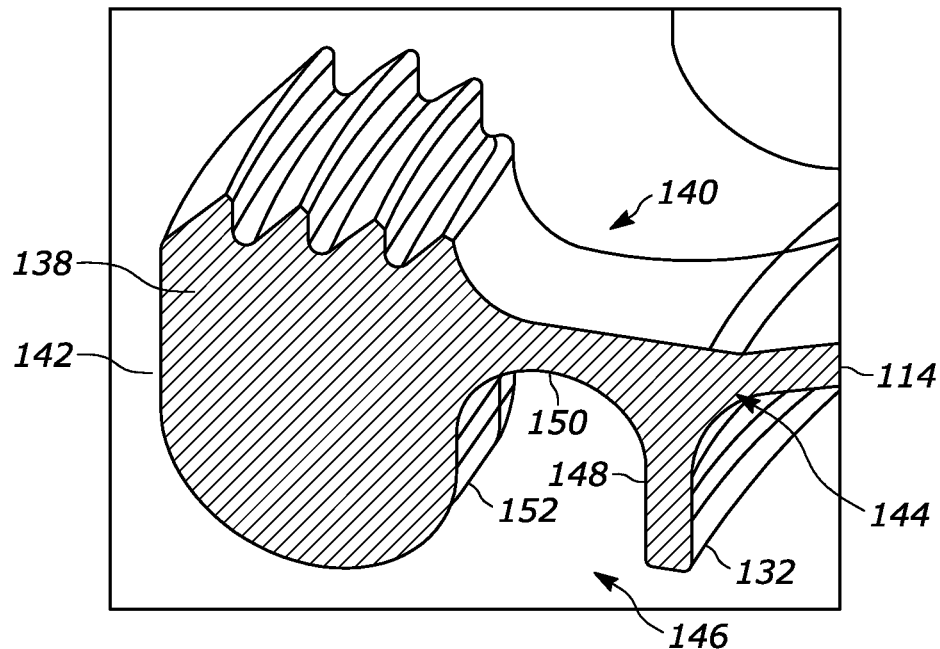
FIG. 18 is a partial cut-away perspective view of part of an IOL according to an aspect of the present disclosure.

Referring to FIGS. 16-18, in an aspect, an IOL 110 is provided comprising a shape-changing optic 112 configured for placement in or adjacent to a lens capsule. IOL 110 has an optical axis extending in an anterior-posterior direction, an equator extending in a plane substantially perpendicular to the optical axis, an accommodated state, a dis-accommodated state, and states therebetween. The optical axis and equator are described above with reference to FIG. 2, for example. IOL 110 comprises an elastic anterior face 114 located anterior to the equator. Anterior face 114 has an anterior surface 116, a posterior surface 118, and a periphery 120. IOL 110 further includes a posterior face 122 located posterior to the equator. Posterior face 122 has an anterior surface 124 defining an annular channel 126, a posterior surface 128, and a periphery 130. IOL 110 further includes an elastic side wall 132 extending across the equator and extending from anterior face 114 to posterior face 122. Side wall 132 further includes a posterior edge 134 complimentary to and non-releasably bonded to annular channel 126 of posterior face 122.

Such an engagement between the posterior edge of the side wall and the annular channel of the posterior face allows for a stronger bond between the anterior face and the posterior face of the optic. In this aspect, when injection molding, the IOL is manufactured in two parts. One part includes the anterior face, the plurality of haptics, and the side wall. The posterior face is molded separately and includes the posterior surface of the posterior face and the annular channel defined by the anterior surface of the posterior face. The annular channel facilitates attaching the posterior face of the IOL to the anterior face. By having the annular channel, the posterior portion (including the posterior edge) of the side wall can fit into annular channel. The annular channel can be partially filled with uncured silicone, silastic material, acrylic, other material, or with a suitable bonding agent for example. The anterior face and the posterior face can then be permanently bonded by curing the silicone or allowing bonding agents to "set," thus forming a sealed chamber.

An advantage of this configuration is that molding the anterior face and the posterior face separately allows the optical surfaces to be highly polished. Molds can be polished to very high optical finish such as, for example, SPI standard A-1 (6000 grit). When components of the IOL are released from the molds, the anterior and posterior surfaces of the anterior face, and the anterior and posterior surfaces of the posterior face can all be highly smooth optical finishes. Because of this, the fluid, for example, filling the chamber does not need to have a refractive index that matches the components of the IOL that define the chamber. For example, the refractive index of silicone, which can be a material that defines the chamber, is approximately 1.41 and silicone oil, which can be material inside the chamber could be 1.51.

Such a configuration of an IOL is more advantageous than configurations of IOLs that are manufactured using blown in molding whereby a single mold is formed and the material is injected (blown in) to adhere to the inner wall of the mold forming the anterior part and posterior part and a chamber as a single unit. This allows for the anterior surface of the anterior part and the posterior surface of the posterior part to have a high-grade optical finish, but the posterior surface of the anterior face and the anterior surface of the posterior face may not have optically smooth finishes (in other words the inside wall which form sthe chamber will not be optically smooth). When this is the case, the optical fluid within the chamber may have a refractive index matched to avoid/limit optical phenomena (such as, e.g. scatter and reflection) which occurs when light passes through the interface of two materials with differing refractive indices.

IOL 110 further includes a chamber 136 located between anterior face 114 and posterior face 122 and containing a material as described above. Anterior face 114 is more resistant to deformational change than the material within the chamber. IOL 110 also includes a plurality of haptics 138 each having a medial portion 140 and a lateral portion 142. The medial portion 140 of each of the haptics extends from and is connected (e.g. directly) to a respective extension site 144 of the periphery 120 of anterior face 114. In addition or alternatively, the IOL can also include an arch 146 located at the extension site 144 or the junction where each of the plurality of haptics extends from and is connected to the anterior face 114 of the optic. In particular, for any given arch 146, the arch is defined by the outer surface 148 of side wall 132, the posterior face 150 of the medial portion 140 of the haptic 138, and the inner surface 152 of the medial portion 140 the haptic 138. Such arches can stabilize the haptics at the extension sites and minimize flexion of the haptics at this junction or extension site.

In particular, the arches can prevent/limit rotation of a haptic at the extension site of the anterior face. This facilitates the haptics extending radially outward allowing the periphery of the haptics to engage the peripheral lens capsule. By maintaining the haptics in a radially oriented fashion, the transfer of radial force by the ciliary muscle/zonules/lens capsule/haptics results in a radial force applied to the anterior face and limits flexion/rotation of the medial portion of the haptics. The arches are configured to prevent haptic rotation yet produce only minimal radial force to the side wall. This can be achieved with the arch having the greatest width at the location where the medial portion of the haptic attaches to the anterior face (the extension site).

The arch defined by the medial portion of the haptic also can facilitate the peripheral portion of the haptic maintaining correct orientation. This allows for optimal fit of the peripheral portion of the haptic into the peripheral lens capsule. The arch can also prevent rotation/flexion of the peripheral portion of the haptic where it joins with the flat portion of the haptic.

Further regarding the haptics, in certain aspects, each of the plurality of haptics can be non-rotatable in response to axial compression along the optical axis on the shape-changing optic. In certain aspects, each of the haptics has a peripheral portion having a posterior face and an anterior face, with the posterior face being curved. In other aspects, the medial portion of each of the plurality of haptics medial portion extends from and is connected to the periphery of the anterior face such that the plurality of haptics changes the shape of the anterior face via application of radial tension to the periphery of the anterior face in a direction perpendicular to the optical axis. For example, the shape change of the anterior face is not via compressive forces along the optical axis on the shape-changing optic.

Figure 19:
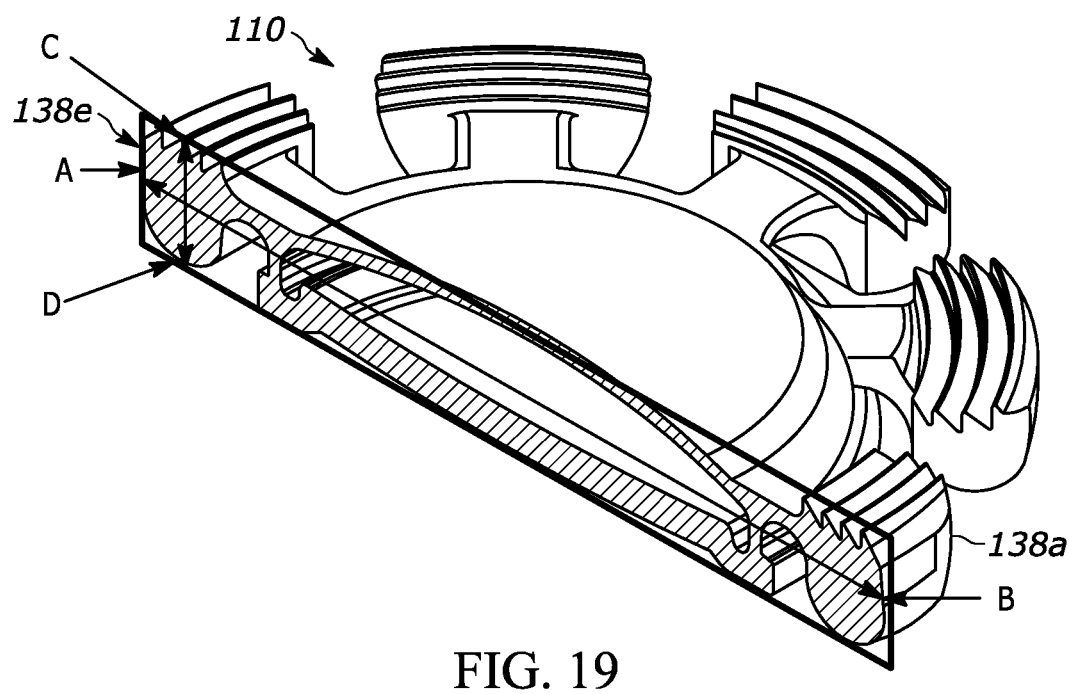
FIG. 19 is a partial cut-away perspective view of part of an IOL according to an aspect of the present disclosure.

Referring to FIG. 19, the IOL can be configured to have a relaxed configuration on the accommodated state. The IOL can be configured such that the haptics are fixated to the lens capsule. As stated above, the zonules attach the lens capsule to the ciliary muscle. When the ciliary muscle relaxes, a force is applied to the lens zonules and this force is translated to the lens capsule and thus to the lens haptics. This radial outward force pulls on the lens haptics which translates the force to the anterior face of the optic, thus decreasing the dioptric power of the optic. If the diameter (A-B) of the IOL were too large or the haptics were too thick (distance C-D) and stretched the lens capsule, increasing the diameter of the lens capsule, the zonules would be relatively slack with relation of the ciliary muscle and the lens capsule. As a result, the zonules may not translate the most optimum force to the lens capsule, and to the haptic arms and therefore the IOL may not change optical power as desired If the diameter (A-B) of the IOL were too small or the haptics were too thin (distance C-D), the IOL may not be stable within the lens capsule and may not maintain a centered position within the lens capsule. To allow for natural variation in lens diameter and thickness, the width of the IOL (distance A-B) or the Anterior-Posterior distance of the haptic (distance C-D), or both, may be varied such that the calculated circumference IOL=will be between approximately 21.0 mm (for eyes that have smaller lenses) and approximately 27.00 mm (for eyes with larger lenses). This can allow the IOL to function properly for eyes of different sized lenses. This can be achieved by varying the diameter measured from points A-B, or by varying the A-P width of the end of the haptic from points C-D.

In another aspect, the IOL can have a circumference calculated as follows: 2× distance (A-B))+2× distance (C-D). Distance A-B is the distance from the most peripheral part of the peripheral surface of one haptic (e.g. 138*e*) (at point A) to the corresponding point on the opposing haptic (e.g. 138*a*) (at point B). Distance C-D is the distance from the most anterior part of a haptic (e.g. 138*a*) (point C) to the most posterior part of the same haptic (e.g. 138*a*) (point D).

The anterior-posterior dimension of each of the haptics can be at least 50% or more (even greater than 100%) than the anterior posterior dimension of the IOL. This provides separation of the anterior and posterior capsule in the periphery and facilitates an advantageous mechanical relationship between the IOL, the haptics, the zonules, and the ciliary muscle.

Each of the disclosed aspects and embodiments of the present disclosure may be considered individually or in combination with other aspects and embodiments as well as with respect to other intra-ocular lenses, such as IOLs disclosed in U.S. patent application Ser. No. 16/288,723 filed on Feb. 28, 2019 and incorporated by reference in its entirety and U.S. Provisional Application No. 62/842,788 filed on May 3, 2019 and incorporated by reference in its entirety. In addition, orientations of a shape-changing optic can be modified. For example, when implanted, the lens can be flipped such that the anterior face is facing in a posterior direction and the posterior face is facing in an anterior direction. Further, the IOL can be configured such that it is foldable for insertion. Further, while certain features of embodiments may be shown in only certain figures, such features can be incorporated into or deleted from other embodiments shown in other figures or otherwise disclosed in the specification. Additionally, when describing a range, all points within that range are included in this disclosure.

What is claimed is:

1. An intraocular lens (IOL) comprising a shape-changing optic configured for placement in or adjacent to a lens capsule, the IOL having an optical axis extending in an anterior-posterior direction, an equator extending in a plane substantially perpendicular to the optical axis, an accommodated state, a dis-accommodated state, and states therebetween, the IOL comprising:
 a posterior face located posterior to the equator, having an anterior surface defining an annular channel, a posterior surface, and a periphery;
 an elastic anterior most face located anterior to the equator, having an anterior surface, a posterior surface, an elastic side wall extending from the posterior surface of the anterior face and having a posterior edge complementary to and non-releasably bonded within the annular channel of the posterior face, and a periphery having a plurality of extension sites;

a chamber located between the anterior face and the posterior face and containing a material, wherein the anterior face is more resistant to deformational change than the material; and a plurality of haptics each having a medial portion and a lateral portion, the medial portion of each of the plurality of haptics extending from and connected to a respective extension site of the plurality of extension sites of the periphery of the anterior face.

2. The IOL of claim 1, wherein the periphery of the posterior face comprises a peripheral edge having a substantially squared configuration.

3. The IOL of claim 1, wherein the side wall is less resistant to deformational change than the anterior face.

4. The IOL of claim 1, wherein the lateral portion of each of the plurality of haptics comprises fixation members configured to engage and fixate to an inner surface of a lens capsule.

5. The IOL of claim 4, wherein the fixation members are alternating raised areas and recessed areas.

6. The IOL of claim 1, wherein each of the plurality of haptics is elastic but is equal to or more resistant to deformational change than the anterior face.

7. The IOL of claim 1, further comprising a plurality of arches, each of which is located at a respective extension site.

8. The IOL of claim 1, wherein each of the plurality of haptics is non-rotatable in response to axial compression along the optical axis of the IOL.

9. The IOL of claim 1, wherein the plurality of haptics extends from and is connected to the respective extension site of the periphery of the anterior face such that the plurality of haptics changes the shape of the anterior face via application of radial tension to the periphery of the anterior face in a direction perpendicular to the optical axis.

10. The IOL of claim 1, wherein each of the plurality of haptics comprises a peripheral portion having a posterior face and an anterior face, the posterior face being curved.

11. The IOL of claim 1, wherein at least one or more of the plurality of haptics comprises a therapeutic agent.

12. An intraocular lens (IOL) comprising a shape-changing optic configured for placement in or adjacent to a lens capsule, the IOL having an optical axis extending in an anterior-posterior direction, an equator extending in a plane substantially perpendicular to the optical axis, an accommodated state, a dis-accommodated state, and states therebetween, the IOL comprising:

an elastic anterior face located anterior to the equator, having an anterior surface, a posterior surface, an elastic side wall extending from the posterior surface, and a periphery having a plurality of extension sites;

a posterior face located posterior to the equator, having an anterior surface, a posterior surface, and a periphery;

a chamber located between the anterior face and the posterior face and containing a material, wherein the anterior face is more resistant to deformational change than the material;

a plurality of haptics each having a medial portion and a lateral portion, the medial portion of each of the plurality of haptics extending from and connected to a respective extension site of the plurality of extension sites of the periphery of the anterior face; and a plurality of arches, each of which is located at a respective extension site of the plurality of extension sites, wherein each of the plurality of arches is defined by an outer surface of the elastic side wall that is integral with the posterior surface of the anterior face of the lens, a posterior face of the medial portion of a respective one of the plurality of haptics, and an inner surface of the medial portion of the respective one of the plurality of haptics, the posterior face of the medial portion located posterior to or at the same level as the anterior face.

13. The IOL of claim 12, wherein each of the plurality of haptics is non-rotatable in response to axial compression of the lens capsule, the axial compression being along the optical axis.

14. The IOL of claim 12, wherein the plurality of haptics extends from and is connected to the respective extension site of the periphery of the anterior face such that the plurality of haptics changes the shape of the anterior face via application of radial tension to the periphery of the anterior face in a direction perpendicular to the optical axis.

15. The IOL of claim 12, wherein each of the plurality of haptics comprises a peripheral portion having a posterior face and an anterior face, the posterior face being curved.

16. The IOL of claim 12, wherein the lateral portion of each of the plurality of haptics comprises fixation members configured to engage and fixate to an inner surface of a lens capsule.

17. The IOL of claim 16, wherein the fixation members are alternating raised areas and recessed areas.

18. The IOL of claim 12, wherein at least one or more of the plurality of haptics comprises a therapeutic agent.

* * * * *